United States Patent
Hernández García et al.

(10) Patent No.: US 11,926,654 B2
(45) Date of Patent: Mar. 12, 2024

(54) FUSION PROTEINS COMPOSED OF AN INTERLEUKIN-2 MUTEIN AND TYPE I INTERFERON

(71) Applicant: CENTRO DE INMUNOLOGIA MOLECULAR, Havana (CU)

(72) Inventors: Tays Hernández García, Havana (CU); Maura Lisett Rábade Chediak, Havana (CU); Kalet León Monzón, Havana (CU); Circe Mesa Pardillo, Havana (CU); Luis Enrique Fernández Molina, Havana (CU); Giselle Hevia Hernández, Havana (CU)

(73) Assignee: CENTRO DE INMUNOLOGIA MOLECULAR, Havana (CU)

( * ) Notice: Subject to any disclaimer, the term of this patent is extended or adjusted under 35 U.S.C. 154(b) by 522 days.

(21) Appl. No.: 17/052,912

(22) PCT Filed: Mar. 5, 2019

(86) PCT No.: PCT/CU2019/050003
§ 371 (c)(1),
(2) Date: Nov. 4, 2020

(87) PCT Pub. No.: WO2019/214757
PCT Pub. Date: Nov. 14, 2019

(65) Prior Publication Data
US 2021/0238246 A1    Aug. 5, 2021

(30) Foreign Application Priority Data
May 7, 2018    (CU) .............................. 2018-000039

(51) Int. Cl.
*C07K 14/56* (2006.01)
*C07K 14/55* (2006.01)
*C12N 15/62* (2006.01)
*A61K 38/00* (2006.01)

(52) U.S. Cl.
CPC .............. *C07K 14/56* (2013.01); *C07K 14/55* (2013.01); *C12N 15/62* (2013.01); *A61K 38/00* (2013.01); *C07K 2319/30* (2013.01)

(58) Field of Classification Search
CPC .... C07K 14/56; C07K 14/55; C07K 2319/30; C12N 15/62; A61K 38/00
See application file for complete search history.

(56) References Cited

U.S. PATENT DOCUMENTS 6,610,830 B1 * 8/2003 Goeddel ................. A61P 31/12
                                                            435/69.51
9,206,243 B2  12/2015 Leon Monzon et al.

FOREIGN PATENT DOCUMENTS

| WO | 2005001025 | A2 | | 1/2005 | | |
|---|---|---|---|---|---|---|
| WO | WO-2012062228 | A2 | * | 5/2012 | ............. | A61K 38/20 |
| WO | WO-2013049234 | A2 | * | 4/2013 | ................ | A61P 3/00 |
| WO | WO-2014100014 | A1 | * | 6/2014 | ......... | A61K 38/2013 |

OTHER PUBLICATIONS

He P. et al, The targeted expression of the human interleukin-2/interferon α2b fused gene in α-fetoprotein-expressing hepatocellular carcinoma cells, J Cancer Res Clin Oncol, 125:77-82, 1999 (Year: 1999).*
Yang C. et al, Engineering of Fc Fragments with Optimized Physicochemical Properties Implying Improvement of Clinical Potentials for Fc-Based Therapeutics, Frontiers in Immunology, 8:1860, Jan. 8, 2018 (Year: 2018).*
Pan H. et al, Methionine oxidation in human IgG2 Fc decreases binding affinities to protein A and FcRn, Protein Science, vol. 18: 424-433, Dec. 29, 2008 (Year: 2008).*
Klein,,J. et al., Design and characterization of structured protein linkers with differing flexibilities, retrieved from:https://doi.org/10.1093/protein/gzu043 (Year: 2014).*
Aron M. Levin et al, "Exploiting a natural conformational switch to engineer an interleukin-2 'superkine'", Nature, (Mar. 25, 2012), vol. 484, No. 7395, doi: 10.1038/nature10975, ISSN 0028-0836, pp. 529-533, XP055214333 [AD] 1-16. DOI: <http://dx.doi.org/10.1038/nature10975>.
Dimitri Flieger et al, "Combinations of the Cytokines IL-12, IL-2 and IFN-[alpha] Significantly Augment Whereas the Cytokine IL-4 Suppresses the Cytokine-Induced Antibody-Dependent Cellular Cytotoxicity of Monoclonal Antibodies 17-1A and BR55-2", Cytokine, US, (Jun. 1, 2000), vol. 12, No. 6, doi:10.1006/cyto.1999.0610, ISSN 1043-4666, pp. 756-761, XP055602099 [AD] 1-16. DOI: <http://dx.doi.org/10.1006/cyto.1999.0610>.
He P et al, "The targeted expression of the human interleukin-2/interferon alpha2b fused gene in alpha-fetoprotein-expressing hepatocellular carcinoma cells.", Journal of Cancer Research and Clinical Oncology 1999, (1999), vol. 125, No. 2, ISSN 0171-5216, pp. 77-82, XP009514290 [XD] 1 p. 78, col. 2 [A] 2-16. DOI: <http://dx.doi.org/10.1007/s004320050245>.

(Continued)

*Primary Examiner* — Adam Weidner
*Assistant Examiner* — Ashley H. Gao
(74) *Attorney, Agent, or Firm* — Banner & Witcoff, Ltd.

(57) ABSTRACT

The present invention describes fusion proteins based on cytokines, called bi-cytokines (BC), specifically formed by the binding of an IL2 agonist mutein with a type I interferon (IFN), linked by an Fc region of a mutant human IgG1 and a connector peptide. The combination of an IL2 agonist mutein and a type I IFN in the structure of the bi-cytokines gives surprising immunoregulatory properties to these molecules and a superior therapeutic effect than that of parental cytokines, or their combination, which makes them attractive and novel molecules for the treatment of cancer. Pharmaceutical compositions comprising as an active ingredient the fusion proteins object of this patent are also described.

17 Claims, 6 Drawing Sheets
Specification includes a Sequence Listing.

(56) References Cited

OTHER PUBLICATIONS

Sonja Steppan et al, "Reduced Secondary Cytokine Induction by BAY 50-4798, a High-Affinity Receptor-Specific Interleukin-2 Analog", Journal of Interferon and Cytokine Research., US, (Mar. 1, 2006), vol. 26, No. 3, doi:10.1089/jir.2006.26.171, ISSN 1079-9907, pp. 171-178, XP055602070 [A] 1-16 BAY 50-4798, mutein of IL-2 (R88N). DOI: <http://dx.doi.org/10.1089/jir.2006.26.171>.
Jul. 24, 2019 (WO) International Search Report—App. PCT/CU2019/050003.

* cited by examiner

FIGURE 1A

CDLPQTHSLGSRRTLMLLAQMRKISLFSCLKDRHDFGFPQEEFGNQFQKAETIPVL
HEMIQQIFNLFSTKDSSAAWDETLLDKFYTELYQQLNDLEACVIQGVGVTETPLMK    SEQ ID NO. 3
EDSILAVRKYFQRITLYLKEKKYSPCAWEVVRAEIMRSFSLSTNLQESLRSKE

FIGURE 1B

AAASDKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKAL    SEQ ID NO. 5
PAPIEKTISKAKGQPREPQVYTLPPSREEVTKNQVSLTCLVKGFYPSDIAVEWESN
GQPENNYKTTPPVLDSDGSFFLYSKLTVDKSRWQQGNVFSCSVMHEALHNHYTQKS
LSLSPGKGGGGSGGGGSGGGGS

FIGURE 2

APTSSSTKKTQLQLEHLLLDLQMILNGINNYKNPKLTRMLTFKFYMP
KKATELKHLQCLEEELKPLEEVLNLAQSKNFHFDPRDVVSNINVFVL    SEQ ID NO. 2
ELKGSETTFMCEYADETATIVEFLNRWITFCQSIISTLT

```
                          SEQUENCE LISTING

<160> NUMBER OF SEQ ID NOS: 12

<210> SEQ ID NO 1
   <211> LENGTH: 133
   <212> TYPE: PRT
   <213> ORGANISM: Artificial Sequence
   <220> FEATURE:
   <223> OTHER INFORMATION: by DNA recombinant technology

<400> SEQUENCE: 1

Ala Pro Thr Ser Ser Ser Thr Lys Lys Thr Gln Leu Gln Leu Glu His
   1               5                   10                  15

Leu Leu Leu Asp Leu Gln Met Ile Leu Asn Gly Ile Asn Asn Tyr Lys
                   20                  25                  30

Asn Pro Lys Leu Thr Ala Met Leu Thr Ala Lys Phe Ala Met Pro Lys
               35                  40                  45

Lys Ala Thr Glu Leu Lys His Leu Gln Cys Leu Glu Glu Ala Leu Lys
       50                  55                  60

Pro Leu Glu Glu Val Leu Asn Leu Ala Gln Ser Lys Asn Phe His Leu
   65                  70                  75                  80

Arg Pro Arg Asp Leu Ile Ser Asn Ile Asn Val Ile Val Leu Glu Leu
                   85                  90                  95

Lys Gly Ser Glu Thr Thr Phe Met Cys Glu Tyr Ala Asp Glu Thr Ala
                   100                 105                 110

Thr Ile Val Glu Phe Leu Asn Arg Trp Ile Thr Phe Ser Gln Ser Ile
               115                 120                 125

Ile Ser Thr Leu Thr
           130

<210> SEQ ID NO 2
   <211> LENGTH: 133
   <212> TYPE: PRT
   <213> ORGANISM: Artificial Sequence
   <220> FEATURE:
   <223> OTHER INFORMATION: by DNA recombinant technology

<400> SEQUENCE: 2

Ala Pro Thr Ser Ser Ser Thr Lys Lys Thr Gln Leu Gln Leu Glu His
   1               5                   10                  15

Leu Leu Leu Asp Leu Gln Met Ile Leu Asn Gly Ile Asn Asn Tyr Lys
                   20                  25                  30

Asn Pro Lys Leu Thr Arg Met Leu Thr Phe Lys Phe Tyr Met Pro Lys
               35                  40                  45

Lys Ala Thr Glu Leu Lys His Leu Gln Cys Leu Glu Glu Glu Leu Lys
       50                  55                  60
```

-continued

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 3
<211> LENGTH: 165
<212> TYPE: PRT
<213> ORGANISM: Artificial Sequence
<220> FEATURE:
<223> OTHER INFORMATION: by DNA recombinant technology

<400> SEQUENCE: 3

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 4
<211> LENGTH: 162
<212> TYPE: PRT
<213> ORGANISM: Artificial Sequence
<220> FEATURE:
<223> OTHER INFORMATION: by DNA recombinant technology

<400> SEQUENCE: 4

Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

```
Leu Asn Leu Phe Thr Ser Lys Asp Leu Ser Ala Thr Trp Asn Ala Thr
 65                  70                  75                  80

Leu Leu Asp Ser Phe Cys Asn Asp Leu His Gln Gln Leu Asn Asp Leu
                 85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
            115                 120                 125

Lys Lys His Ser Leu Cys Ala Trp Glu Val Ile Arg Ala Glu Val Trp
        130                 135                 140

Arg Ala Leu Ser Ser Ser Thr Asn Leu Leu Ala Arg Leu Ser Glu Glu
145                 150                 155                 160

Lys Glu

<210> SEQ ID NO 5
<211> LENGTH: 246
<212> TYPE: PRT
<213> ORGANISM: Artificial Sequence
<220> FEATURE:
<223> OTHER INFORMATION: by DNA recombinant technology

<400> SEQUENCE: 5

Ala Ala Ala Ser Asp Lys Thr His Thr Cys Pro Pro Cys Pro Ala Pro
  1               5                  10                  15

Glu Ala Ala Gly Gly Pro Ser Val Phe Leu Phe Pro Pro Lys Pro Lys
             20                  25                  30

Asp Thr Leu Met Ile Ser Arg Thr Pro Glu Val Thr Cys Val Val Val
             35                  40                  45

Asp Val Ser His Glu Asp Pro Glu Val Lys Phe Asn Trp Tyr Val Asp
         50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Glu Val Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys Gly Gly Gly Gly Ser Gly Gly Gly Gly
225                 230                 235                 240

Ser Gly Gly Gly Gly Ser
                245
```

<210> SEQ ID NO 6
<211> LENGTH: 544
<212> TYPE: PRT
<213> ORGANISM: Artificial Sequence
<220> FEATURE:
<223> OTHER INFORMATION: by DNA recombinant technology

<400> SEQUENCE: 6

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Ala Ala Ala Ser Asp Lys Thr His Thr Cys Pro
                165                 170                 175

Pro Cys Pro Ala Pro Glu Ala Ala Gly Gly Pro Ser Val Phe Leu Phe
            180                 185                 190

Pro Pro Lys Pro Lys Asp Thr Leu Met Ile Ser Arg Thr Pro Glu Val
        195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Glu Glu Val Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365
```

```
Gly Asn Val Phe Ser Cys Ser Val Met His Glu Ala Leu His Asn His
            370             375                 380

Tyr Thr Gln Lys Ser Leu Ser Leu Ser Pro Lys Gly Gly Gly Gly Gly
385                 390                 395                 400

Ser Gly Gly Gly Ser Gly Gly Gly Ser Ala Pro Thr Ser Ser
                405             410                 415

Ser Thr Lys Lys Thr Gln Leu Gln Leu Glu His Leu Leu Leu Asp Leu
            420                 425                 430

Gln Met Ile Leu Asn Gly Ile Asn Asn Tyr Lys Asn Pro Lys Leu Thr
                435                 440                 445

Ala Met Leu Thr Ala Lys Phe Ala Met Pro Lys Lys Ala Thr Glu Leu
450                 455                 460

Lys His Leu Gln Cys Leu Glu Glu Ala Leu Lys Pro Leu Glu Glu Val
465                 470                 475                 480

Leu Asn Leu Ala Gln Ser Lys Asn Phe His Leu Arg Pro Arg Asp Leu
                485                 490                 495

Ile Ser Asn Ile Asn Val Ile Val Leu Glu Leu Lys Gly Ser Glu Thr
                500                 505                 510

Thr Phe Met Cys Glu Tyr Ala Asp Glu Thr Ala Thr Ile Val Glu Phe
            515                 520                 525

Leu Asn Arg Trp Ile Thr Phe Ser Gln Ser Ile Ile Ser Thr Leu Thr
530                 535                 540

<210> SEQ ID NO 7
<211> LENGTH: 544
<212> TYPE: PRT
<213> ORGANISM: Artificial Sequence
<220> FEATURE:
<223> OTHER INFORMATION: by DNA recombinant technology

<400> SEQUENCE: 7

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Ala Ala Ala Ser Asp Lys Thr His Thr Cys Pro
                165                 170                 175

Pro Cys Pro Ala Pro Glu Ala Ala Gly Gly Pro Ser Val Phe Leu Phe
            180                 185                 190
```

```
Pro Pro Lys Pro Lys Asp Thr Leu Met Ile Ser Arg Thr Pro Glu Val
            195                 200                 205

Thr Cys Val Val Val Asp Val Ser His Glu Asp Pro Glu Val Lys Phe
    210                 215                 220

Asn Trp Tyr Val Asp Gly Val Glu Val His Asn Ala Lys Thr Lys Pro
225                 230                 235                 240

Arg Glu Glu Gln Tyr Asn Ser Thr Tyr Arg Val Val Ser Val Leu Thr
                245                 250                 255

Val Leu His Gln Asp Trp Leu Asn Gly Lys Glu Tyr Lys Cys Lys Val
            260                 265                 270

Ser Asn Lys Ala Leu Pro Ala Pro Ile Glu Lys Thr Ile Ser Lys Ala
        275                 280                 285

Lys Gly Gln Pro Arg Glu Pro Gln Val Tyr Thr Leu Pro Pro Ser Arg
    290                 295                 300

Glu Glu Val Thr Lys Asn Gln Val Ser Leu Thr Cys Leu Val Lys Gly
305                 310                 315                 320

Phe Tyr Pro Ser Asp Ile Ala Val Glu Trp Glu Ser Asn Gly Gln Pro
                325                 330                 335

Glu Asn Asn Tyr Lys Thr Thr Pro Pro Val Leu Asp Ser Asp Gly Ser
            340                 345                 350

Phe Phe Leu Tyr Ser Lys Leu Thr Val Asp Lys Ser Arg Trp Gln Gln
        355                 360                 365

Gly Asn Val Phe Ser Cys Ser Val Met His Glu Ala Leu His Asn His
    370                 375                 380

Tyr Thr Gln Lys Ser Leu Ser Leu Ser Pro Gly Lys Gly Gly Gly Gly
385                 390                 395                 400

Ser Gly Gly Gly Gly Ser Gly Gly Gly Ser Ala Pro Thr Ser Ser
                405                 410                 415

Ser Thr Lys Lys Thr Gln Leu Gln Leu Glu His Leu Leu Leu Asp Leu
            420                 425                 430

Gln Met Ile Leu Asn Gly Ile Asn Asn Tyr Lys Asn Pro Lys Leu Thr
        435                 440                 445

Arg Met Leu Thr Phe Lys Phe Tyr Met Pro Lys Lys Ala Thr Glu Leu
    450                 455                 460

Lys His Leu Gln Cys Leu Glu Glu Leu Lys Pro Leu Glu Glu Val
465                 470                 475                 480

Leu Asn Leu Ala Gln Ser Lys Asn Phe His Phe Asp Pro Arg Asp Val
                485                 490                 495

Val Ser Asn Ile Asn Val Phe Val Leu Glu Leu Lys Gly Ser Glu Thr
            500                 505                 510

Thr Phe Met Cys Glu Tyr Ala Asp Glu Thr Ala Thr Ile Val Glu Phe
        515                 520                 525

Leu Asn Arg Trp Ile Thr Phe Cys Gln Ser Ile Ile Ser Thr Leu Thr
    530                 535                 540

<210> SEQ ID NO 8
<211> LENGTH: 536
<212> TYPE: PRT
<213> ORGANISM: Artificial Sequence
<220> FEATURE:
<223> OTHER INFORMATION: by DNA recombinant technology

<400> SEQUENCE: 8

Cys Asp Leu Pro His Thr Tyr Asn Leu Gly Asn Lys Arg Ala Leu Thr
1               5                   10                  15
```

-continued

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Ala Glu Val Trp
    130                 135                 140

Arg Ala Leu Ser Ser Thr Asn Leu Leu Ala Arg Leu Ser Glu Glu
145                 150                 155                 160

Lys Glu Ala Ala Ala Ser Gly Cys Lys Pro Cys Ile Cys Thr Val Pro
                165                 170                 175

Glu Val Ser Ser Val Phe Ile Phe Pro Pro Lys Pro Lys Asp Val Leu
            180                 185                 190

Thr Ile Thr Leu Thr Pro Lys Val Thr Cys Val Val Val Ala Ile Ser
        195                 200                 205

Lys Asp Asp Pro Glu Val Gln Phe Ser Trp Phe Val Asp Asp Val Glu
210                 215                 220

Val His Thr Ala Gln Thr Gln Pro Arg Glu Glu Gln Phe Asn Ser Thr
225                 230                 235                 240

Phe Arg Ser Val Ser Glu Leu Pro Ile Met His Gln Asp Trp Leu Asn
                245                 250                 255

Gly Lys Glu Phe Lys Cys Arg Val Asn Ser Ala Ala Phe Pro Ala Pro
            260                 265                 270

Ile Glu Lys Thr Ile Ser Lys Thr Lys Gly Arg Pro Lys Ala Pro Gln
        275                 280                 285

Val Tyr Thr Ile Pro Pro Lys Glu Gln Met Ala Lys Asp Lys Val
    290                 295                 300

Ser Leu Thr Cys Met Ile Thr Asp Phe Phe Pro Glu Asp Ile Thr Val
305                 310                 315                 320

Glu Trp Gln Trp Asn Gly Gln Pro Ala Glu Asn Tyr Lys Asn Thr Gln
                325                 330                 335

Pro Ile Met Asp Thr Asp Gly Ser Tyr Phe Val Tyr Ser Lys Leu Asn
            340                 345                 350

Val Gln Lys Ser Asn Trp Glu Ala Gly Asn Thr Phe Thr Cys Ser Val
        355                 360                 365

Leu His Glu Gly Leu His Asn His His Thr Glu Lys Ser Leu Ser His
    370                 375                 380

Ser Pro Gly Lys Gly Gly Gly Ser Gly Gly Gly Ser Gly Gly
385                 390                 395                 400

Gly Gly Ser Ala Pro Thr Ser Ser Ser Thr Lys Lys Thr Gln Leu Gln
                405                 410                 415

Leu Glu His Leu Leu Leu Asp Leu Gln Met Ile Leu Asn Gly Ile Asn
            420                 425                 430

Asn Tyr Lys Asn Pro Lys Leu Thr Ala Met Leu Thr Ala Lys Phe Ala

```
                    435                 440                 445
Met Pro Lys Ala Thr Glu Leu Lys His Leu Gln Cys Leu Glu Glu
    450                 455                 460

Ala Leu Lys Pro Leu Glu Glu Val Leu Asn Leu Ala Gln Ser Lys Asn
465                 470                 475                 480

Phe His Leu Arg Pro Arg Asp Leu Ile Ser Asn Ile Asn Val Ile Val
                485                 490                 495

Leu Glu Leu Lys Gly Ser Glu Thr Thr Phe Met Cys Glu Tyr Ala Asp
            500                 505                 510

Glu Thr Ala Thr Ile Val Glu Phe Leu Asn Arg Trp Ile Thr Phe Ser
            515                 520                 525

Gln Ser Ile Ile Ser Thr Leu Thr
            530                 535

<210> SEQ ID NO 9
<211> LENGTH: 536
<212> TYPE: PRT
<213> ORGANISM: Artificial Sequence
<220> FEATURE:
<223> OTHER INFORMATION: by DNA recombinant technology

<400> SEQUENCE: 9

Cys Asp Leu Pro His Thr Tyr Asn Leu Gly Asn Lys Arg Ala Leu Thr
1               5                   10                  15

Val Leu Glu Glu Met Arg Arg Leu Pro Pro Leu Ser Cys Leu Lys Asp
            20                  25                  30

Arg Lys Asp Phe Gly Phe Pro Leu Glu Lys Val Asp Asn Gln Gln Ile
        35                  40                  45

Gln Lys Ala Gln Ala Ile Leu Val Leu Arg Asp Leu Thr Gln Gln Ile
    50                  55                  60

Leu Asn Leu Phe Thr Ser Lys Asp Leu Ser Ala Thr Trp Asn Ala Thr
65                  70                  75                  80

Leu Leu Asp Ser Phe Cys Asn Asp Leu His Gln Gln Leu Asn Asp Leu
                85                  90                  95

Lys Ala Cys Val Met Gln Glu Pro Pro Leu Thr Gln Glu Asp Ser Leu
            100                 105                 110

Leu Ala Val Arg Thr Tyr Phe His Arg Ile Thr Val Tyr Leu Arg Lys
        115                 120                 125

Lys Lys His Ser Leu Cys Ala Trp Glu Val Ile Arg Ala Glu Val Trp
    130                 135                 140

Arg Ala Leu Ser Ser Ser Thr Asn Leu Leu Ala Arg Leu Ser Glu Glu
145                 150                 155                 160

Lys Glu Ala Ala Ala Ser Gly Cys Lys Pro Cys Ile Cys Thr Val Pro
                165                 170                 175

Glu Val Ser Ser Val Phe Ile Phe Pro Pro Lys Pro Lys Asp Val Leu
            180                 185                 190

Thr Ile Thr Leu Thr Pro Lys Val Thr Cys Val Val Val Ala Ile Ser
        195                 200                 205

Lys Asp Asp Pro Glu Val Gln Phe Ser Trp Phe Val Asp Asp Val Glu
    210                 215                 220

Val His Thr Ala Gln Thr Gln Pro Arg Glu Glu Gln Phe Asn Ser Thr
225                 230                 235                 240

Phe Arg Ser Val Ser Glu Leu Pro Ile Met His Gln Asp Trp Leu Asn
                245                 250                 255

Gly Lys Glu Phe Lys Cys Arg Val Asn Ser Ala Ala Phe Pro Ala Pro
```

```
            260                 265                 270
Ile Glu Lys Thr Ile Ser Lys Thr Lys Gly Arg Pro Lys Ala Pro Gln
        275                 280                 285

Val Tyr Thr Ile Pro Pro Lys Glu Gln Met Ala Lys Asp Lys Val
    290                 295                 300

Ser Leu Thr Cys Met Ile Thr Asp Phe Phe Pro Glu Asp Ile Thr Val
305                 310                 315                 320

Glu Trp Gln Trp Asn Gly Gln Pro Ala Glu Asn Tyr Lys Asn Thr Gln
                325                 330                 335

Pro Ile Met Asp Thr Asp Gly Ser Tyr Phe Val Tyr Ser Lys Leu Asn
            340                 345                 350

Val Gln Lys Ser Asn Trp Glu Ala Gly Asn Thr Phe Thr Cys Ser Val
        355                 360                 365

Leu His Glu Gly Leu His Asn His His Thr Glu Lys Ser Leu Ser His
    370                 375                 380

Ser Pro Gly Lys Gly Gly Gly Ser Gly Gly Gly Gly Ser Gly Gly
385                 390                 395                 400

Gly Gly Ser Ala Pro Thr Ser Ser Thr Lys Lys Thr Gln Leu Gln
                405                 410                 415

Leu Glu His Leu Leu Leu Asp Leu Gln Met Ile Leu Asn Gly Ile Asn
            420                 425                 430

Asn Tyr Lys Asn Pro Lys Leu Thr Arg Met Leu Thr Phe Lys Phe Tyr
        435                 440                 445

Met Pro Lys Lys Ala Thr Glu Leu Lys His Leu Gln Cys Leu Glu Glu
    450                 455                 460

Glu Leu Lys Pro Leu Glu Glu Val Leu Asn Leu Ala Gln Ser Lys Asn
465                 470                 475                 480

Phe His Phe Asp Pro Arg Asp Val Val Ser Asn Ile Asn Val Phe Val
                485                 490                 495

Leu Glu Leu Lys Gly Ser Glu Thr Thr Phe Met Cys Glu Tyr Ala Asp
            500                 505                 510

Glu Thr Ala Thr Ile Val Glu Phe Leu Asn Arg Trp Ile Thr Phe Cys
        515                 520                 525

Gln Ser Ile Ile Ser Thr Leu Thr
    530                 535

<210> SEQ ID NO 10
<211> LENGTH: 1563
<212> TYPE: DNA
<213> ORGANISM: Artificial Sequence
<220> FEATURE:
<223> OTHER INFORMATION: by DNA recombinant technology

<400> SEQUENCE: 10
tgcgatctgc cccacaccta caacctgggc aacaagagag ccctgaccgt gctggaggag    60
atgaggagac tgcctcctct gtcctgcctg aaggacagga aggacttcgg cttccccctg   120
gagaaggtgg acaaccagca gatccagaag gcccaggcta tcctggtgct gagagacctg   180
acacagcaga tcctgaacct gttcacctcc aaggacctgt ctgccacctg gaatgccacc   240
ctgctggact ccttctgcaa cgacctgcac cagcagctga cgacctgaa ggcctgcgtg   300 atgcaggagc tcctctgac ccaggaggat tctctgctgg ctgtgcggac ctacttccac    360
cggatcaccg tgtacctgcg gaagaagaag cactctctgt gcgccctggga ggtgatcaga   420 gccgaagtgt ggagagccct gtcctcctct accaacctgc tggccaggct gtctgaggag   480
```

-continued

| | | | | |
|---|---|---|---|---|
| aaggaggcgg | ccgcttctgg | ttgtaagcct | tgcatatgta | cagtcccaga | agtatcatct | 540 |
| gtcttcatct | tccccccaaa | gcccaaggat | gtgctcacca | ttactctgac | tcctaaggtc | 600 |
| acgtgtgttg | tggtagccat | cagcaaggat | gatcccgagg | tccagttcag | ctggtttgta | 660 |
| gatgatgtgg | aggtgcacac | agctcagacg | caaccccggg | aggagcagtt | caacagcact | 720 |
| ttccgctcag | tcagtgaact | tcccatcatg | caccaggact | ggctcaatgg | caaggagttc | 780 |
| aaatgcaggg | tcaacagtgc | agctttccct | gccccatcg | agaaaaccat | ctccaaaacc | 840 |
| aaaggcagac | cgaaggctcc | acaggtgtac | accattccac | ctcccaagga | gcagatggcc | 900 |
| aaggataaag | tcagtctgac | ctgcatgata | acagacttct | tccctgaaga | cattactgtg | 960 |
| gagtggcagt | ggaatgggca | gccagcggag | aactacaaga | acactcagcc | catcatggac | 1020 |
| acagatggct | cttacttcgt | ctacagcaag | ctcaatgtgc | agaagagcaa | ctgggaggca | 1080 |
| ggaaatactt | tcacctgctc | tgtgttacat | gagggcctgc | acaaccacca | tactgagaag | 1140 |
| agcctctccc | actctcctgg | taaagccccc | acctccagca | gcaccaagaa | aactcagctc | 1200 |
| cagctcgaac | atctgctgct | ggatctgcag | atgatcctga | acggcatcaa | caactacaag | 1260 |
| aaccccaagc | tgaccgccat | gctgacagcc | aagttcgcca | tgcccaagaa | ggccaccgag | 1320 |
| ctgaagcatc | tgcagtgcct | ggaagaggcc | ctgaagcctc | tggaagaggt | gctgaacctg | 1380 |
| gcccagtcca | gaacttcca | cctgaggccc | agggacctga | tcagcaacat | caacgtgatc | 1440 |
| gtgctggaac | tgaagggcag | cgagacaacc | ttcatgtgcg | agtacgccga | cgagacagca | 1500 |
| acaatcgtgg | agtttctgaa | ccggtggatc | accttcagcc | agagcatcat | cagcacctg | 1560 |
| acc | | | | | | 1563 |

<210> SEQ ID NO 11
<211> LENGTH: 1632
<212> TYPE: DNA
<213> ORGANISM: Artificial Sequence
<220> FEATURE:
<223> OTHER INFORMATION: by DNA recombinant technology

<400> SEQUENCE: 11

| | | | | | |
|---|---|---|---|---|---|
| tgcgatctgc | cgcagaccca | tagcctgggc | agccgccgca | ccctgatgct | gctggcgcag | 60 |
| atgcgcaaaa | ttagcctgtt | tagctgcctg | aaagatcgcc | atgattttgg | ctttccgcag | 120 |
| gaagaatttg | caaccagtt | tcagaaagcg | gaaaccattc | cggtgctgca | tgaaatgatt | 180 |
| cagcagattt | ttaacctgtt | tagcaccaaa | gatagcagcg | cggcgtggga | tgaaaccctg | 240 |
| ctggataaat | tttataccga | actgtatcag | cagctgaacg | atctggaagc | gtgcgtgatt | 300 |
| cagggcgtgg | gcgtgaccga | aaccccgctg | atgaaagaag | atagcattct | ggcggtgcgc | 360 |
| aaatattttc | agcgcattac | cctgtatctg | aagaaaaaa | aatatagccc | gtgcgcgtgg | 420 |
| gaagtggtgc | gcgcggaaat | tatgcgcagc | tttagcctga | gcaccaacct | gcaggaaagc | 480 |
| ctgcgcagca | aagaagcggc | cgctagcgac | aaaactcaca | catgcccacc | gtgcccagca | 540 |
| cctgaagccg | cggggggacc | gtcagtcttc | ctcttccccc | caaaacccaa | ggacaccctc | 600 |
| atgatctccc | ggaccctga | ggtcacatgc | gtggtggtgg | acgtgagcca | cgaagaccct | 660 |
| gaggtcaagt | tcaactggta | cgtggacggc | gtggaggtgc | ataatgccaa | gacaaagccg | 720 |
| cgggaggagc | agtacaacag | cacgtaccgt | gtggtcagcg | tcctcaccgt | cctgcaccag | 780 |
| gactggctga | atggcaagga | gtacaagtgc | aaggtctcca | acaaagccct | cccagccccc | 840 |
| atcgagaaaa | ccatctccaa | agccaaaggg | cagccccgag | aaccacaggt | gtacaccctg | 900 |
| cccccatccc | gggaggagt | gaccaagaac | caggtcagcc | tgacctgcct | ggtcaaaggc | 960 |

-continued

```
ttctatccca gcgacatcgc cgtggagtgg gagagcaatg ggcagccgga gaacaactac      1020
aagaccacgc ctcccgtgct ggactccgac ggctccttct tcctctatag caagctcacc      1080
gtggacaaga gcaggtggca gcaggggaac gtcttctcat gctccgtgat gcatgaggct      1140
ctgcacaacc actacacgca gaagtcgctc agcctgtccc cgggtaaagg tggaggcggt      1200
tcaggcggag gtggttctgg cggtggcgga tcggcgccga ccagcagcag caccaaaaaa      1260
acccagctgc agctggaaca tctgctgctg gatctgcaga tgattctgaa cggcattaac      1320
aactataaaa acccgaaact gacccgcatg ctgacccttta aatttttatat gccgaaaaaa      1380 gcgaccgaac tgaaacatct gcagtgcctg gaagaagaac tgaaaccgct ggaagaagtg      1440
ctgaacctgg cgcagagcaa aaactttcat tttgatccgc gcgatgtggt gagcaacatt      1500
aacgtgtttg tgctggaact gaaaggcagc gaaaccacct ttatgtgcga atatgcggat      1560
gaaaccgcga ccattgtgga atttctgaac cgctggatta ccttttgcca gagcattatt      1620
agcaccctga cc                                                         1632
```

<210> SEQ ID NO 12
<211> LENGTH: 241
<212> TYPE: PRT
<213> ORGANISM: Artificial Sequence
<220> FEATURE:
<223> OTHER INFORMATION: by DNA recombinant technology

<400> SEQUENCE: 12

```
Ala Ala Ala Ser Gly Cys Lys Pro Cys Ile Cys Thr Val Pro Glu Val
1               5                   10                  15

Ser Ser Val Phe Ile Phe Pro Pro Lys Pro Lys Asp Val Leu Thr Ile
            20                  25                  30

Thr Leu Thr Pro Lys Val Thr Cys Val Val Val Ala Ile Ser Lys Asp
        35                  40                  45

Asp Pro Glu Val Gln Phe Ser Trp Phe Val Asp Val Glu Val His
    50                  55                  60

Thr Ala Gln Thr Gln Pro Arg Glu Glu Gln Phe Asn Ser Thr Phe Arg
65                  70                  75                  80

Ser Val Ser Glu Leu Pro Ile Met His Gln Asp Trp Leu Asn Gly Lys
                85                  90                  95

Glu Phe Lys Cys Arg Val Asn Ser Ala Ala Phe Pro Ala Pro Ile Glu
            100                 105                 110

Lys Thr Ile Ser Lys Thr Lys Gly Arg Pro Lys Ala Pro Gln Val Tyr
        115                 120                 125

Thr Ile Pro Pro Pro Lys Glu Gln Met Ala Lys Asp Lys Val Ser Leu
    130                 135                 140

Thr Cys Met Ile Thr Asp Phe Phe Pro Glu Asp Ile Thr Val Glu Trp
145                 150                 155                 160

Gln Trp Asn Gly Gln Pro Ala Glu Asn Tyr Lys Asn Thr Gln Pro Ile
                165                 170                 175

Met Asp Thr Asp Gly Ser Tyr Phe Val Tyr Ser Lys Leu Asn Val Gln
            180                 185                 190

Lys Ser Asn Trp Glu Ala Gly Asn Thr Phe Thr Cys Ser Val Leu His
        195                 200                 205
```

```
Glu Gly Leu His Asn His His Thr Glu Lys Ser Leu Ser His Ser Pro
    210             215                 220

Gly Lys Gly Gly Gly Gly Ser Gly Gly Gly Gly Ser Gly Gly Gly Gly
225             230                 235                 240

Ser
```

FUSION PROTEINS COMPOSED OF AN INTERLEUKIN-2 MUTEIN AND TYPE I INTERFERON

CROSS-REFERENCE TO RELATED APPLICATIONS

This application is a U.S. National Stage of International Application No. PCT/CU2019/050003, filed May 3, 2019, which claims priority from Application 2018-000039 filed on May 7, 2018 in Cuba. The entire contents of these applications are incorporated herein by reference in their entirety.

SCOPE OF THE TECHNIQUE

The present invention relates to the field of Biotechnology and Immuno-oncology, especially to the development of fusion proteins based on cytokines. Particularly it describes fusion proteins composed by the binding of a type I interferon (IFN) to interleukin 2 (IL2) agonist muteins.

BACKGROUND

Despite decades of hard work in the field of cancer immunotherapy, related to the use of cytokines, the results obtained so far have been modest. The high toxicity and reduced half-life of these molecules, as well as the low percentage of benefited patients, make it necessary to create innovative strategies that enhance their antitumor properties, which will translate into better quality and longer life of cancer patients. Among the mechanisms that undermine the therapeutic efficacy of cytokines is the induction of regulatory T cells, which suppress the response of cytotoxic CD8+ T cells in the tumor microenvironment (Ovens and Naugler (2012) Theoretical Biology and Medical Modeling, 9: 44).

Traditionally, combinations have been one of the strategies aimed at optimizing the therapeutic use of cytokines in the treatment of cancer, either through the co-administration of soluble molecules or the generation of fusion proteins, often called fusokines. Among the advantages associated with the use of the latter, are not only the feasibility of their production, but also the possibility of establishing stoichiometric relationships between molecules with different pharmacological properties. In addition, it has been shown that some fusokines have a superior therapeutic effect as compared to the administration of parental cytokines separately, and even when compared to their combination (Stagg J. et al (2004) Cancer Research, 64: 8795-8799; Acres B. (2005) Cancer Research, 65: 9536-9546); US 2011/0150828. One of the therapeutic strategies recently described in the study of fusokines is the intratumoral administration of mRNA encoding a fusion protein based on type 1 IFN and the ectodomain of the TGFβ receptor, which showed antitumor effect. The technology of intratumoral transfer of mRNA is a highly versatile, reproducible, easy and adaptable therapeutic tool well suited for the clinical scenario (Van der Jeught et al (2015), Oncolmmunology, 4: 5).

Two cytokines relevant for the antitumor therapy are a type 1 interferon: IFNα, and IL2, which are potent inducers of T helper 1 response patterns desired in the treatment of cancer. The direct antitumor action of IFNα on malignant cells has been previously described. It has been associated to cytostatic, antiproliferative effect and to a decrease in extracellular matrix protease levels, which are involved in the processes of invasion and metastasis and related to a worse prognosis of the disease. On the other hand, this cytokine promotes the maturation and migration of antigen presenting cells, the induction of cross-presentation in αCD8 dendritic cells and lymphocytes activation (Chikkala et al (1990) Cancer Research, 50: 1176-1182). It has been described that IFNα protects T cells from mitochondria-dependent apoptosis, as a consequence of the activation mediated by the antigen, and thus favors the process of clonal expansion, in a regulated manner (Dondi et al (2004) The Journal of Immunology, 173 (6): 3740-3747).

On the other hand, the cytokine IL2 is an autocrine factor that promotes the proliferation of antigen activated T lymphocytes. However, it binds with higher affinity to regulatory T lymphocytes than to effector cells, thus inducing their proliferation with the consequent negative impact in the antitumor effect (Chaput et al (2007). J Immunol, 179: 4969-4978). One of the strategies to improve the therapeutic efficacy of this molecule is the development of muteins based on a rational design. Such is the case of the IL2 agonist mutein generated in the Center of Molecular Immunology, which is unable to bind to the high affinity receptor expressed in regulatory T cells. The IL2 agonist mutein will be hereinafter referred to as no alpha IL2 (SEQ ID NO 6 of U.S. Pat. No. 9,206,243). As a result of its modifications with respect to wild-type IL2, no alpha IL2 preferentially expands effector populations of NK and memory CD8 T cells, over regulatory T lymphocytes. The lower toxicity of this molecule on healthy tissues in comparison with wild type 112 has also been described (Carmenate et al (2013). of Immunology, 190: 6230-6238).

Another agonist variant of IL2 was generated from in vitro evolution (genetic engineering). This variant named superkine of IL2 (H9) exhibits increased binding affinity for the beta chain of the IL2 receptor and stimulates a powerful proliferation of the T lymphocytes, independently of the expression of CD25 alpha chain of IL2 receptor. In fact, it has been shown that it is able to induce an increased expansion of cytotoxic T lymphocytes, an enhanced antitumor response in vivo, a limited expansion of regulatory T cells, and reduced toxicity, with respect to IL2 (Levin et al. (2012) Nature, 48: 529-535). This variant will be hereinafter referred to as H9.

Several studies suggest a synergistic effect of the combined administration of IL2 and IFNα in the treatment of cancer. The ability to stimulate antibody-dependent cellular cytotoxicity induced by BR55-2 MAb against the HT29 colorectal carcinoma line was significantly increased by using the combination of IFNα and IL2, as compared to that of cytokines used separately (Flieger et al. (2000) Cytokine, 12: 756-761). In 2010, Konjevic et al., demonstrated that both IL2 and IFNα increase the in vitro activity of NK cells, from peripheral blood samples taken from clinical stage IV metastatic melanoma patients. Both cytokines, IL2 and IFNα, were able to stimulate the expression of NKG2D activating receptor in NK cells, even in the subpopulation of NK cells with high expression of CD16; NKG2D induction by both cytokines correlated with the induction of NK cell activity (Konjevic et al (2010) Melanoma Research, 20: 459-67).

In the literature there is a report describing the generation of a fusion protein that combines two cytokines, wild type IL2 and human IFNα2b. In this molecule, IL2 is directly linked to IFNα2b, and its antitumor effect was not compared with that of parental cytokines and their combination (He et al (1999) J Leukoc Biol, 125: 77-82), so there is no evidence of its superiority over them.

Taking into account the antecedents described above, the inventors of the present application generated several bifunctional fusion proteins called bi-cytokines (BC), for cancer therapy. Two bifunctional molecules that combine a type I IFN with IL2 agonists were obtained for the treatment of cancer. To obtain them, the starting point was the fusion of two muteins: no alpha IL-2 or H9, and IFNα. The proposed design for these BC, hereinafter referred to as BC2 and BC3, respectively, consists of the connection of both cytokines through an Fc region of an immunoglobulin with limited binding to Fcγ receptors. The presence of this Fc region, capable of binding to neonatal Fc receptors, allows to increase the half-life time. These combinations and design constitute novel elements in the development of this type of proteins. The resulting molecules have immunomodulatory effect, as well as surprising in vivo antitumor properties, which are superior to those observed after the administration of each parental cytokine (fused to the same Fc region), and even, to the combination of these, in equimolar amounts.

BRIEF DESCRIPTION OF THE INVENTION

In one embodiment, the subject of the present invention is fusion proteins comprising an IL2 mutein connected through a linker to a type I IFN. Particularly, the sequences of the IL2 muteins that are part of the fusion proteins of the present invention are described in SEQ ID NO 1 and 2. The IFN that is part of the structure of said fusion proteins is IFNα (SEQ ID NO 3).

In a particular embodiment the fusion proteins of the present invention are characterized in that the linker consists of an Fc region of a mutated human IgG1, and a connector peptide, and its sequence is shown in SEQ ID NO 5.

Additionally, the sequences of the fusion proteins described in the present invention are shown in SEQ ID NO 6 and 7, and the nucleic acid sequences encoding them are shown in SEQ ID NOs 10 and 11, respectively.

In another embodiment, the present invention relates to pharmaceutical compositions comprising as active ingredient the fusion proteins described in SEQ ID NO 6 and 7, and a pharmaceutically acceptable carrier.

In another embodiment, the subject of the present invention is the use of the fusion proteins described herein in the treatment of cancer; including the intratumoral injection approach of the nucleic acid molecules encoding said fusion proteins.

DETAILED DESCRIPTION OF THE INVENTION

Design of the BCs

The fusion proteins of the present invention were designed taking into account the pathological scenario for which they were intended. BC2 is formed by the fusion of the no alpha IL-2 mutein, whose sequence is shown in SEQ ID NO. 1 (previously disclosed in SEQ ID No. 6 of U.S. Pat. No. 9,206,243 B2) with the human IFNα whose sequence is shown in FIG. 1A and in SEQ ID. NO 3 of the present invention. The Fc region of a mutated human IgG1 having the L234A L235A mutations, associated with a limited capacity of activation of receptors involved in the immune response (Hezareh et al (2001) J Virol., 75 (24): 12161-12168), and the connector peptide $(Gly_4Ser)_3$ form the linker element. The IFNα molecule is bound at the N-terminal end (Nt) of the linker fragment, and the no alpha IL2 molecule at the C-terminal end (Ct). The sequence of said linker is described in FIGS. 1B and 1n SEQ ID. NO 5.

BC3 is formed by the fusion of human IFNα, whose sequence is shown in FIGS. 1A and 1n SEQ ID. NO 3, to the aforementioned H9 mutein, whose sequence is shown in SEQ ID NO. 2 and FIG. 2. The linker element is composed by the Fc region of a human IgG1 with mutations L234A L235A, and a limited activation capacity of receptors involved in the immune response, and the linker peptide $(Gly_4Ser)_3$. The IFNα molecule is bound at the Nt of the linker fragment and at the Ct it is found the H9 molecule. The sequence of said linker is described in FIGS. 1B and 1n SEQ ID. NO 5.

Pharmaceutical Compositions

The BC object of the present invention can be found as active ingredient, forming part of different pharmaceutical compositions suitable therefore, and a pharmaceutically acceptable carrier. The concentrations of the active ingredient in said pharmaceutical compositions are within the range from 1 μg/ml to 20 μg/ml, preferably from 5 μg/ml to 10 μg/ml.

The pharmaceutically acceptable carriers include, but are not limited to: saline solution, phosphate buffered saline pH neutral, and similar formulations. Other buffering agents, dispersing agents, and non-toxic inert substances suitable for administration to a patient may be included in the compositions of the present invention. The compositions may be suitable solutions for administration, and are normally sterile and free of undesirable particles.

Therapeutic Use and Treatment

The novel format of the BC is partially due to the presence of an Fc region in the linker element of the cytokines that compose them. This Fc region makes possible its purification by protein A affinity chromatography, which allows the administration as a soluble protein by different routes (subcutaneous, intravenous, intradermal, intramuscular, intraperitoneal) and also, increases the half-life times of these agents in circulation and thus, improves their therapeutic effectiveness. This allows the use of lower doses with the consequent reduction of toxicity. An alternative route of administration is the intratumoral, which would have a lower toxicity as compared with the other routes. Likewise, the presence of no alpha IL2 or H9 is associated to reduced toxicity in comparison with the wild-type IL2 molecule, currently used in the clinical scenario.

In addition, the administration strategies used in the present invention for these BC may include intratumoral injection of the product, by gene-based therapeutic approaches, for example, the intratumoral injection of mRNA and transducing particles encoding them. The genetic modification of the tumor or infiltrating tumor cells, for the expression of BC2 or BC3, guarantees the presence of these in the tumor microenvironment, which makes possible its immunomodulatory action as well as the direct effect on the tumor itself. The versatility and high reproducibility of the intratumoral injection of nucleic acids encoding therapeutic agents is a suitable platform for the treatment of different types of tumors. Given the immunomodulatory properties of these molecules, in addition to the potentiation of the antitumor response in situ in a non-specific manner, the stimulation of the specific antigen immune response, supported by the possible combination with targeted therapies in patients with various types of cancer can be considered for future treatments.

In this way, the aforementioned BC aim to constitute a new therapeutic front that enhances the pharmacological action of the type I IFN and the IL2 individual cytokines, currently used in the treatment of cancer. This effect would be associated with the preferential expansion of cytotoxic T cells over regulatory T cells, which leads to a more efficient antitumor immune response, and therefore, to a delay in tumor growth and a greater survival of the treated individuals. In addition to this, the lower levels of toxicity of the IL2 muteins used, increase the likelihood of success in comparison with that of the therapies with wild type cytokines. All these responses can be translated into greater life expectancy and quality of life in the patients treated.

BRIEF DESCRIPTION OF THE FIGURES

FIG. 1. Sequence of: (A) human IFNα2b, (B) linker fragment.
FIG. 2. Sequence of H9.

Figure 3:
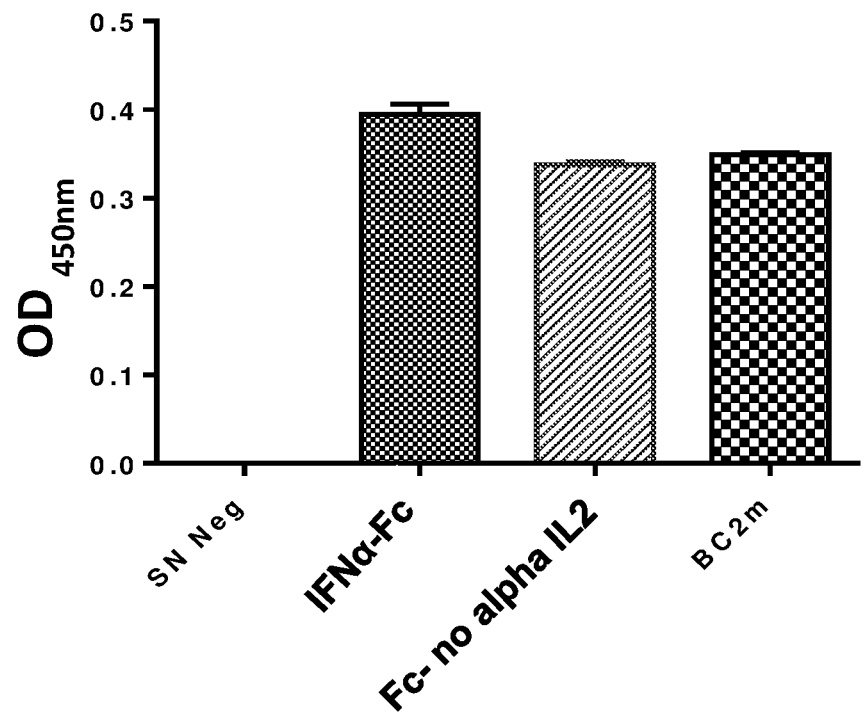
FIG. 3. Evaluation of transient expression of the BC2m and the single controls in HEK293T cells by ELISA.

The present invention is further elaborated with the following examples and figures. However, these examples should not be construed as limiting the scope of the invention.

EXAMPLES

Example 1. Design and Obtainment of the BCs and Single Controls of Cytokines

For modeling in mice the immunomodulatory and antitumor effect of the BCs based on type I IFN and IL2 agonists, the BC2m described in SEQ ID NO 8 was generated. This consists of a type I IFN, the murine IFNα4 (SEQ. ID NO 4), fused to the no alpha IL2 mutein, example of IL2 agonist, described in SEQ ID NO 1, through a linker fragment shown in SEQ ID NO 12, which consists of an Fc region of a mutated murine IgG1 bound to the peptide connector (Gly$_4$Ser)$_3$. The D265A mutation in the Fc region reduces the activation capacity of the receptors involved in the immune response (Becker J. C. et al (1996) PNAS, 93: 2702-2707). The no alpha IL2 mutein is located towards the Ct terminal of the linker fragment, whereas the IFNα4 is located at the Nt terminal of this same fragment. Therefore, the BC2m is a dimeric and tetravalent molecule.

The single controls were designed as molecules containing each parental cytokine fused to the Fc region of the mutated murine IgG1 (D265A), and maintaining the relative positions of each cytokine in the BC2m structure. Thus, in the single IFNα control, this cytokine was bound to the Nt of the above mentioned Fc region, whereas in the single control of no alpha IL2, this cytokine is located towards the Ct of the above referred Fc region. Thus, the single controls of IFNα and no alpha IL2 are dimeric, and bivalent molecules.

The BC2m and the single controls IFNα-Fc and Fc-no alpha IL2 genes were cloned in the pLV-CMV-IRES-Neo vector for transient expression assays in higher cells. The resulting genetic constructions also served as transfer vectors for obtaining the transducing particles used in the genetic modification of the tumor cell lines. The expression of said genes in HEK293T cells was checked by transient transfection using lipofectamine. The quantification of the different recombinant molecules in the supernatants was carried out by means of an ELISA specific for the murine Fc region.

Generation of BC2 and BC3

For the construction of the BC2 and BC3 human BCs, human IFNα (SEQ ID NO 3 and FIG. 1A) and the agonist muteins no alpha IL2 and H9, described in SEQ ID NO. 1 and 2, respectively, were used. The Fc region of a mutated human IgG1 with L234A L235A mutations and limited activation capacity of receptors involved in the immune response, and the linker peptide (Gly$_4$Ser)$_3$ were used as a linker; said linker is shown in SEQ ID NO. 5 and FIG. 1B. The IFNα molecule is bound at the Nt of the linker fragment, and the no alpha IL2 or the H9, at the Ct of the linker.

The final designs of the bifunctional proteins BC2 and BC3 are shown in SEQ ID NO. 6 and 7, respectively. The genes of BC2 and BC3 were cloned in the transfer vector pLV-CMV-IRES-Neo, for stable expression in higher cells. The functionality of these genes was checked by transient expression assays with lipofectamine in HEK293T cells, for which the recombinant molecules were quantified by an ELISA specific for the human Fc region.

Example 2. BC2m is Expressed as an Integral and Functional Protein

Once the BC2m constructs and the single controls IFNα-Fc and Fc-no alpha IL2 were obtained, a transient transfection assay was performed on HEK293T cells to evaluate the feasibility of the design of these molecules. After 72 hours of culture, the supernatants were removed and an ELISA specific for the murine Fc region was performed. For this, polystyrene plates were coated with an antibody specific for the murine IgG molecule and incubated with the supernatants of cells transfected with each of the constructs containing the genes of BC2m and the single controls. Finally, the detection was carried out using an antibody specific for the Fc region of a murine IgG, conjugated to the enzyme peroxidase. From the interpolation of the absorbance values at 492 nm in a standard curve with a murine IgG, the concentrations of the recombinant proteins were calculated. By means of this test it was possible to detect the expression of the three proteins of interest, and the functionality of the designed format was checked (FIG. 3).

Figure 4A:
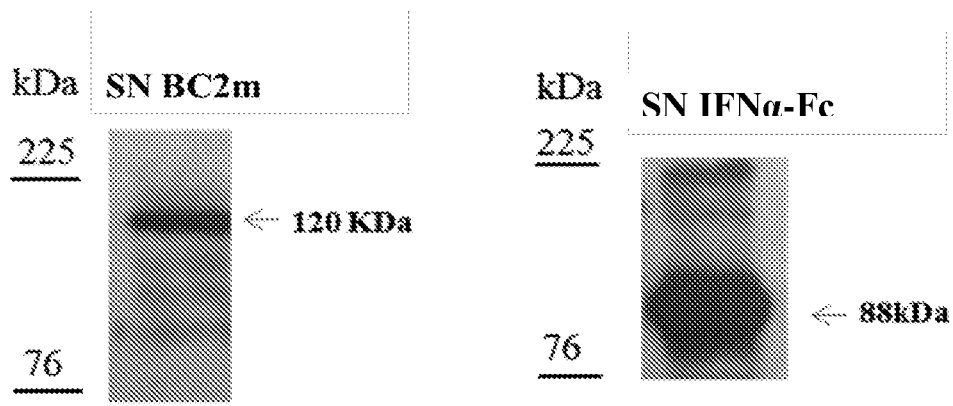
FIG. 4. Immunoidentification by Western blot of the BC2m and the single controls, with: (A) an antibody specific for IFNα, (B) an antibody specific for IL2.
Figure 4B:
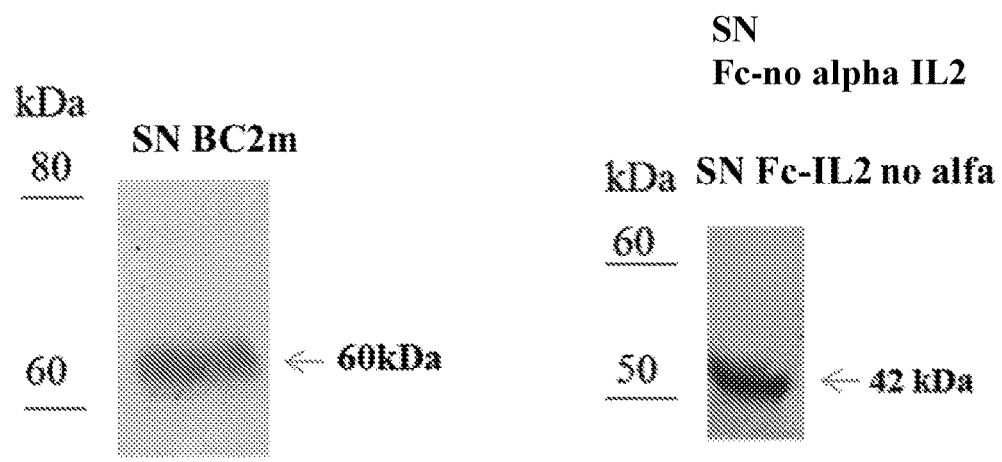

Similarly, by performing a Western blot assay specific for cytokines IFNα and IL2, the presence thereof in the structure of the BC2m was checked (FIGS. 4A and B). Likewise, it was verified that BC2m was expressed as a protein whose electrophoretic migration corresponds to the theoretical size of 120 kDa, for the dimer, and 60 kDa for the monomer, under non-reducing and reducing conditions, respectively. The identification of these cytokines was also checked in the corresponding single controls IFNα-Fc and Fc-no alpha IL2, and the electrophoretic migrations detected correspond to the expected sizes according to the design (FIGS. 4A and 4B).

Example 3. BC2m Preserves the Biological Activities Corresponding to the Cytokines IFNα and IL2

Figure 5A:
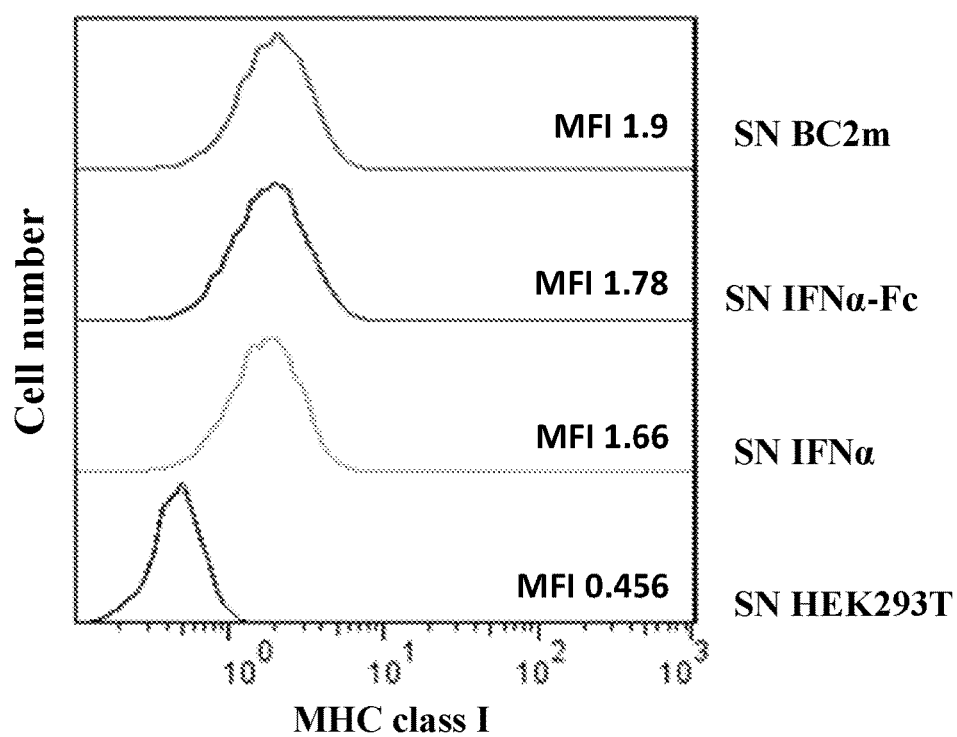
FIG. 5. (A) IFNα-like activity of BC2m and IFNα-Fc control, as measured by the test of induction of MHCI expression in MB16F10 tumor cells treated with supernatants of transfected HEK293T cells, (B) IL2-like activity of the BC2m and the single control Fc-no alpha IL2, as measured by the test of expansion of T CD8+ lymphocytes, from cultures of splenocytes of naive mice, treated with supernatants of transfected HEK293T cells.

To determine whether the portions of IFNα4 and the no alpha IL2 mutein were active in the structure of the BC2m and the single controls, in vitro experiments were performed with the supernatants of HEK293T cells transfected with the corresponding genetic constructs, and using equimolar amounts of the molecules. The supernatant of non-transfected HEK293T cells was used as a negative control. In the case of the IFNα-like activity, the increase in the expression of MHCI on the surface of MB16F10 melanoma cells treated during 24 hours with said supernatants, was evaluated by flow cytometry. The supernatants containing the BC2m or the IFNα-Fc control were able to stimulate the expression of MHCI in the treated tumor cells, in contrast with the results obtained using the negative control, which indicates that the activity functionality of IFNα is preserved in the structure of the BC2 (FIG. 5A).

To determine whether the no alpha IL2 present in the BC2m and the Fc-no alpha IL2 control exhibited biological activity, a CD8+ lymphocyte proliferation stimulation assay was performed with splenocytes cultures from naive mice. Splenocytes from C57BL/6 mice were labeled with the CFSE reagent and cultured for 72 hours, in the presence of the supernatants of transfected HEK293T cells containing the BC2m or the Fc-no alpha IL2 control. At the end of the experiment, the percentage of CD8+ T lymphocytes in proliferation was analyzed. As a negative control, splenocytes incubated with a supernatant of non-transfected HEK293T cells were used, and the Proliferation Ratio of CD8+ T Lymphocytes (Pr) was calculated by dividing the percentage of proliferating CD8+ T cells for the splenocytes treated with the BC2m or the Fc-no alpha IL2, and the value corresponding to the negative control, respectively.

Figure 5B:
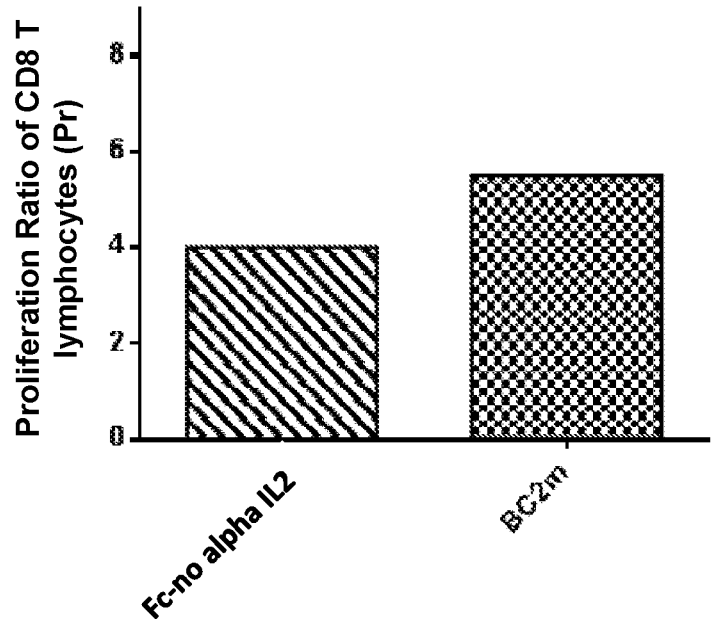

In FIG. 5B the supernatants containing the BC2 and the Fc-no alpha IL2, were able to induce splenocyte proliferation, 4 and 5 times more than the negative control, respectively. These results demonstrate that the no alpha IL2 portion contained in the structure of said fusion proteins retains its biological properties.

Figure 6A:
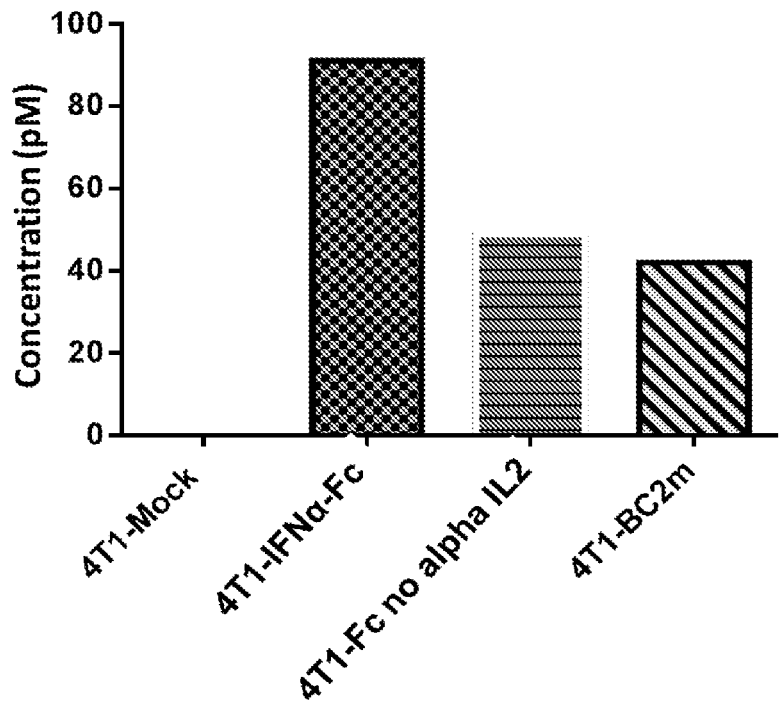
FIG. 6. Detection of the BC2m and the single controls in the supernatant of transduced 4T1 tumor cells by ELISA (A) specific for the Fc region. (B) specific for the Fc and IL2 regions, (C) specific for the Fc and IFNα regions.

Example 4. BC2m is Secreted by 4T1 Tumor Cells Genetically Modified by Lentiviral Transduction To evaluate the antitumor activity of the BC2m in vivo, the approach of transduced tumor cells was selected, using as a model the 4T1 mammary carcinoma. The cells were transduced with lentiviral particles encoding the BC2m and the single controls. As negative control, tumor cells transduced with the empty pLV-CMV-IRES-Neo vector (mock control) were used. The transduced cells were maintained in selective medium (with G-418 antibiotic) for 10 days, and the concentration of the recombinant molecules in the supernatants was measured by ELISA to detect the Fc portion of murine immunoglobulins. The BC2m and the single controls were detected by this technique in the supernatants of the transduced tumor cells (FIG. 6A).

Figure 6B:
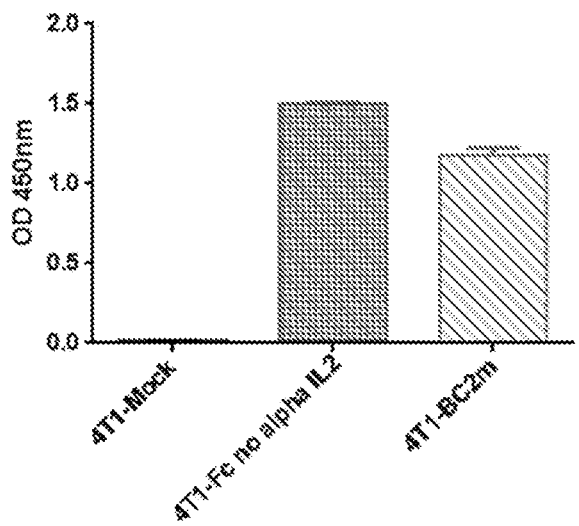
Figure 6C:
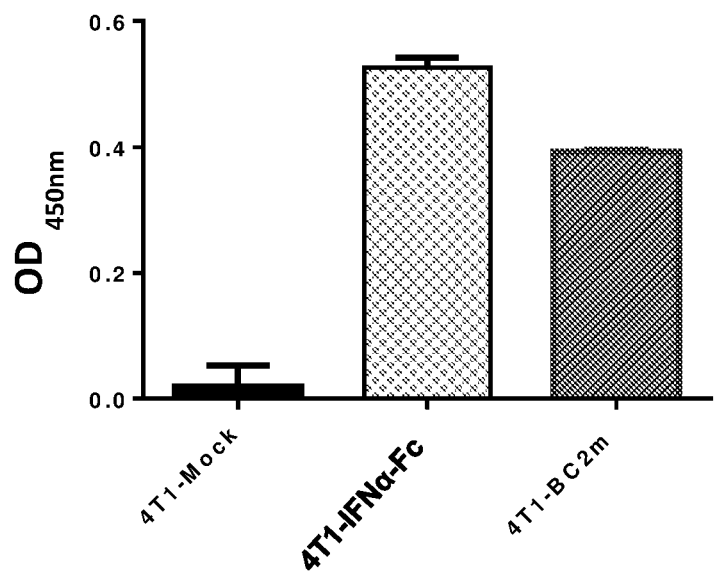

In addition, the presence of the no alpha IL2 portion and IFNα in the BC2m and the single controls was confirmed by sandwich ELISAs. In one of them, the supernatants of the transduced cells were incubated on plates coated with an anti-Fc antibody, and the IL2 portion was detected with the sequential addition of a rabbit antibody specific for the IL2 and an anti-rabbit immunoglobulin antibody conjugated to the enzyme peroxidase. Thus, the Fc-IL2 portion was detected in the structure of the BC2m and the single Fc-no alpha IL2 control (FIG. 6B). In another assay, the supernatants of the transduced cells were incubated on plates coated with an anti-IFNα antibody, and the Fc portion was detected with an antibody specific for the Fc region of a mouse IgG, conjugated to the enzyme peroxidase. The IFNα-Fc portion was detected in the BC2m and the single IFNα-Fc control (FIG. 6C).

Example 5. The BC2m Shows an Antitumor Effect Superior to that of the Controls of Individual Cytokines IFNα-Fc and Fc-No Alpha IL2, or their Combination For comparing the antitumor effect of the BC2m with respect to that of the controls, it was evaluated the growth of the implanted tumors from the 4T1 cells secreting the different molecules. Five groups of animals to be treated were conceived: three of them received 4T1-Mock, 4T1-IFNα-Fc or 4T1-Fc-no alpha IL2 cells, and the remaining two groups were inoculated with a combination of no alpha 4T1-IFNα-Fc+4T1-FcIL2 or 4T1-BC2m cells. A number of 100 000 total cells were administered subcutaneously. Considering that the transduced lines expressed different levels of recombinant proteins, they were mixed in some cases with mock cells to ensure that the secreted protein/total cell ratio was equivalent among all the groups.

For the analysis of the results, paired comparisons of the frequencies of animals with tumors of less or equal volume than the smallest found in the 4T1-Mock group were performed among the different groups, by means of Fisher's exact test, on days 25 and 27 of the experiment.

Figure 7:
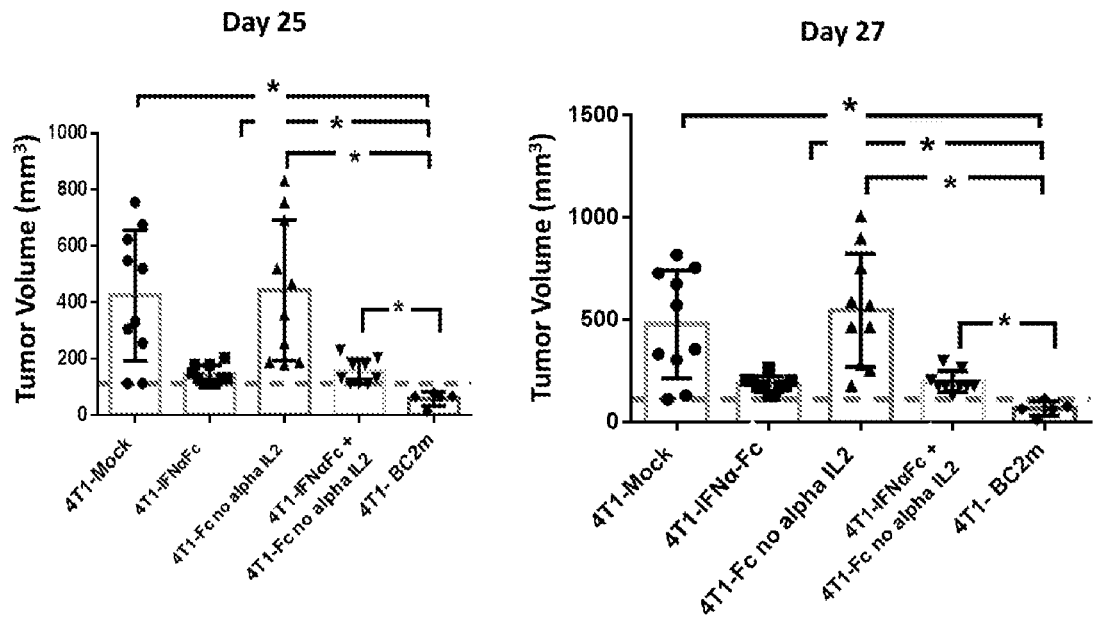
FIG. 7. Evaluation of the antitumor effect of BC2m by using transduced 4T1 tumor cells, on days 25 and 27 of the experiment.

As observed in FIG. 7, the frequency of animals with tumors of less or equal size than the lowest value observed in the Mock control group was significantly higher in the group that received 4T1-BC2m cells, as compared with the single individual controls and their combination, on days 25 and 27 (Fisher's exact test, $p<0.05$). This phenomenon was not observed in the group that received the combination of 4T1-IFNα-Fc+4T1-Fc no alpha IL2 cells, in which the frequency evaluated is not different in comparison with the groups treated with each of the monotherapies (results not shown, Fisher's exact test, $p>0.05$). These results point to the therapeutic superiority of BC2m because they indicate that the binding of the IFNα to the no alpha IL2, leads to the activation of qualitatively or quantitatively different molecular and cellular mechanisms, which exert an enhanced antitumor response, higher than that obtained with the co-administration of the single controls of cytokines IFNα-Fc and Fc-no alpha IL2, or the administration of these cytokines individually.

Figure 8:
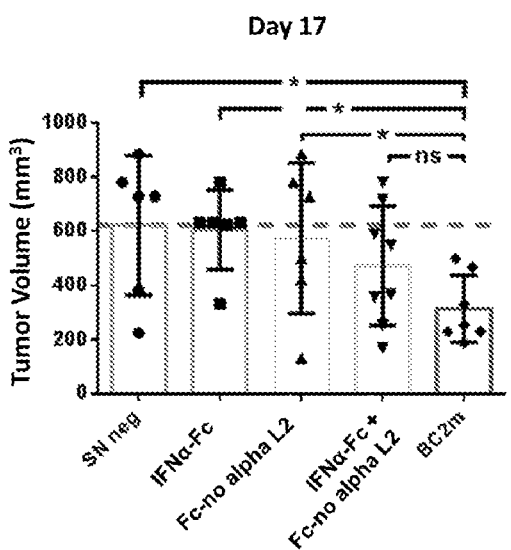
FIG. 8. Evaluation of the therapeutic effect in the 4T1 model of the intratumoral injection of the BC2m, at day 17 of the experiment.

Example 6. The Intratumoral Injection of the BC2m has a Greater Antitumor Effect than that of Single Controls IFNα-Fc and Fc-No Alpha IL2 in the 4T1 Model 4T1 cells were inoculated in BALB/c immunocompetent mice. After 10 days, equimolar amounts of IFNα-Fc, Fc-no alpha IL2 and BC2m, contained in supernatants of previously transfected HEK293T cells, were injected intratumorally. An additional group received the injection of the mixture of supernatants containing IFNα-Fc and Fc-no alpha IL2, thus ensuring the equimolarity of each of the cytokines, with respect to the single controls and the BC2m. As a negative control, the supernatant of non-transfected HEK293T cells was used. The supernatants were injected with a daily frequency, for four days. As seen in FIG. 8, at day 17 of the experiment, 100% of the mice treated with the BC2m had tumor volumes below the mean of the negative control group, a result that was not observed in any other treatment group. The frequency of animals bearing tumors with lower size than the mean of the negative control group was higher in the group treated with BC2m than in any of the groups receiving the individual therapies IFNα-Fc or Fc-no alpha IL2 (Fisher's exact test; $p<0.05$). However, the frequency of animals with tumor volumes smaller than the mean tumor volume of the negative control group, was higher in the group treated with the combination of the IFNα-Fc and Fc-no alpha IL2 controls, than that of the single control IFNα-Fc. In contrast, this frequency was not higher with respect to the Fc-no alpha IL2 control, which points the need of binding IFNα and no alpha IL2 cytokines in the same molecule to achieve a more efficient protective effect. This could be due to the possible activation of molecular and cellular mechanisms associated with the simultaneous stimulation of the receptors of both molecules. Overall, these evidences support the superior therapeutic value of local administration of the BC2m in the tumor, with respect to parental cytokines.

The invention claimed is:

1. A fusion protein comprising an IL2 agonist mutein linked to a human interferon (IFN) α by a linker, wherein the linker consists of a mutated human IgG1 Fc region and a connector peptide.

2. The fusion protein according to claim 1, wherein the IL2 agonist mutein has the sequence shown in SEQ ID NO 1.

3. The fusion protein according to claim 1, wherein the IL2 agonist mutein has the sequence shown in SEQ ID NO 2.

4. The fusion protein according to claim 1, wherein the human IFNα has the sequence shown in SEQ ID NO 3.

5. The fusion protein according to claim 1, wherein the linker has the sequence shown in SEQ ID NO 5.

6. The fusion protein according to claim 1, having the sequence shown in SEQ ID NO 6.

7. The fusion protein according to claim 1, having the sequence shown in SEQ ID NO 7.

8. A nucleic acid molecule comprising a nucleotide sequence having the sequence shown in SEQ ID NO 10 encoding the fusion protein of claim 6.

9. A nucleic acid molecule comprising a nucleotide sequence having the sequence shown in SEQ ID NO 11 encoding the fusion protein of claim 7.

10. An mRNA molecule encoding the fusion protein of claim 6.

11. An mRNA molecule encoding the fusion protein of claim 7.

12. A pharmaceutical composition comprising as active ingredient the fusion protein of claim 6, in a concentration range from 1 μg/ml to 20 μg/ml, and a pharmaceutically acceptable carrier.

13. A pharmaceutical composition comprising as active ingredient the fusion protein of claim 7, in a concentration range from 1 μg/ml to 20 μg/ml, and a pharmaceutically acceptable carrier.

14. A method of treating cancer in a subject in need thereof comprising administering to the subject a therapeutically effective amount of the fusion protein of claim 6.

15. A method of treating cancer in a subject in need thereof comprising administering to the subject a therapeutically effective amount of the fusion protein of claim 7.

16. A method of treating cancer in a subject in need thereof comprising administering to the subject a therapeutically effective amount of the nucleic acid molecule of claim 8 by intratumoral injection.

17. A method of treating cancer in a subject in need thereof comprising administering to the subject a therapeutically effective amount of the nucleic acid molecule of claim 9 by intratumoral injection.

* * * * *

UNITED STATES PATENT AND TRADEMARK OFFICE
CERTIFICATE OF CORRECTION

| | |
|---|---|
| PATENT NO. | : 11,926,654 B2 |
| APPLICATION NO. | : 17/052912 |
| DATED | : March 12, 2024 |
| INVENTOR(S) | : Tays Hernández García et al. |

Page 1 of 1

It is certified that error appears in the above-identified patent and that said Letters Patent is hereby corrected as shown below:

On the Title Page

Column 1; Item (22); PCT Filed:
Please delete "Mar. 5, 2019" and insert --May 3, 2019--

Signed and Sealed this
First Day of October, 2024

Katherine Kelly Vidal
*Director of the United States Patent and Trademark Office*